(12) United States Patent
Dennerlein et al.

(10) Patent No.: US 8,428,216 B2
(45) Date of Patent: Apr. 23, 2013

(54) METHOD FOR RECONSTRUCTION OF A THREE-DIMENSIONAL IMAGE DATA SET AND X-RAY DEVICE

(75) Inventors: Frank Dennerlein, Forchheim (DE); Bernhard Scholz, Heroldsbach (DE)

(73) Assignee: Siemens Aktiengesellschaft, München ( * ) Notice: Subject to any disclaimer, the term of this patent is extended or adjusted under 35 U.S.C. 154(b) by 125 days.

(21) Appl. No.: 13/176,957

(22) Filed: Jul. 6, 2011

(65) Prior Publication Data

US 2012/0008740 A1    Jan. 12, 2012

(30) Foreign Application Priority Data

Jul. 7, 2010    (DE) .......................... 10 2010 026 374

(51) Int. Cl.
*A61B 6/00*        (2006.01)
(52) U.S. Cl.
USPC .............................................. 378/4; 382/131
(58) Field of Classification Search ....... 378/4; 382/131
See application file for complete search history.

(56) References Cited

U.S. PATENT DOCUMENTS

| | | | | |
|---|---|---|---|---|
| 6,148,056 A | * | 11/2000 | Lin et al. | ............................ 378/4 |
| 7,430,270 B2 | * | 9/2008 | Bontus et al. | .................... 378/17 |
| 7,477,720 B2 | * | 1/2009 | Pack et al. | .......................... 378/4 |
| 7,756,315 B2 | * | 7/2010 | Hsieh et al. | .................... 382/131 |
| 8,306,304 B2 | * | 11/2012 | Noo et al. | ..................... 382/131 |
| 2009/0016592 A1 | * | 1/2009 | Hoppe et al. | ................. 382/131 |

FOREIGN PATENT DOCUMENTS

| DE | 102008031530 A1 | 1/2009 |
|---|---|---|
| WO | WO 2007004196 A2 | 1/2007 |

OTHER PUBLICATIONS

Feldkamp et al.; "Practical Cone-beam Algorithm"; JOSA A1, 612 (1984); J. Opt. Soc. Amer. A, vol. 1, No. 6, Jun. 1984, pp. 612-619; Journal of the Optical Society of America.

* cited by examiner

*Primary Examiner* — Alexander H Taningco

(57) ABSTRACT

A method for reconstruction of a three-dimensional image data set from projection images of an object captured with an X-ray device from different projection angles is proposed. At least one sub-area of the object is outside the coverage of the X-ray device, or as a result of strong attenuation by a metal so that no projection data is present in the sub-area. Filter lines are determined n the projection images. A first local transformation is performed along the filter lines on the projection images. The missing projection data on the transformed projection data is augmented. A non-local transformation is performed on the transformed projection data for determining of filtered, augmented projection data. The non-local transformation is different from a ramp filter which is created by the first local transformation and the non-local transformation. The three-dimensional image data set is determined by backprojection of the filtered, augmented projection data.

15 Claims, 2 Drawing Sheets

METHOD FOR RECONSTRUCTION OF A THREE-DIMENSIONAL IMAGE DATA SET AND X-RAY DEVICE

CROSS REFERENCE TO RELATED APPLICATIONS

This application claims priority of German application No. 10 2010 026 374.5 filed Jul. 7, 2010, which is incorporated by reference herein in its entirety.

FIELD OF THE INVENTION

The invention relates to a method for reconstruction of a three-dimensional image data set from a multiplicity of projection images of an object captured with an X-ray device from different projection angles, wherein from at least one sub-area of the object to be captured in the case of a sub-area lying outside the coverage of the X-ray device, or as a result of strong attenuation, in particular by means of metal, no projection data is present in the sub-area.

BACKGROUND OF THE INVENTION

In particular in the field of three-dimensional computed tomography (CT), but also in the case of other X-ray devices, methods are known to calculate a spatial density distribution of an object, for example of a patient or of an industrial object, from projection images captured from different projection angles, thus a three-dimensional image data set. For reconstructions of this kind, reconstruction algorithms of filtered back projection (FBP) are frequently employed. These algorithms are efficient and robust, and are based essentially on the following computation steps.

Initially a weighting of the projection images is conventionally performed, thus a cosine weight and/or redundancy weight are introduced, in order correctly to evaluate the projection data according to its ultimate contribution. Accordingly, filter lines are identified in the projection images, along which a filtering is subsequently to take place. This procedure is widely known; if, for example, the projection images are captured along a circular path (circular CT), then lines running horizontally on the detector are generally selected.

After the filter lines are known, a one-dimensional filtering of the projection data takes place along the filter lines with a high-pass kernel, wherein a ramp filter is used in most cases. The projection data thus filtered is then finally back-projected weighted three-dimensionally into the volume, in order to obtain the three-dimensional image data set.

Such filtered back-projection algorithms are widely known; one of the best known and most frequently used algorithms is the so-called Feldkamp algorithm, cf. here thus the article by L. A. Feldkamp, L. C. Davis and J. W. Kress, "Practical cone-beam algorithm", J. Opt. Soc. Am. A 1(6), 1984.

In practice—in particular in medical imaging, in non-destructive materials testing or also in security scanners—the projection data is frequently fully known to the effect that the entire object is mapped by means thereby, which means that there exist sub-areas of the object for which the projection data is missing. For example many objects cannot be captured to their complete extent by means of the detector used with the X-ray device (so-called data truncation). However captured projection image areas can basically be completely unusable for the reconstruction, as they for example lie in the shadow of a strongly attenuating metal inserts and thus contain no further information which is sensibly usable the reconstruction (metal artifacts). For the purposes of the present invention it is assumed that such present but unusable projection data can be understood as missing projection data of the object.

In the case of such missing projection data, the problem occurs that the projection image defects are initially distributed along the filter line during the high-pass filtering, where they are then transferred to the image result by means of the back-projection, and generate unwanted artifacts (truncation artifacts, metal artifacts).

In order to reduce truncation artifacts in the use of the Feldkamp algorithm or in similar FBP algorithms, the projection data extrapolation or projection data interpolation method is generally employed. This method is based on two steps: the areas are initially identified, in which projection data defects, i.e. missing projection data, are present. Subsequently, for example, metal regions or truncation edges are identified. The missing projection data within the identified areas is estimated herefrom, for example by means of data interpolation or smooth extrapolation, possibly after a preceding homogenization of the projection images, cf. here for example J. Müller, T. Buzug "Intersection Line Length Normalization in CT Projection Data", in: Bildverarbeitung fair die Medizin, Springer-Verlag, pages 77-81, 2008.

These steps can essentially be regarded as a pre-processing of the projection images, because the conventional Feldkamp algorithm is then used. Although this leads to an artifact reduction of the reconstructed images, from the practical perspective it involves disadvantageous modifications, in particular in relation to maintenance, implementation and computational efficiency, as ultimately an additional pre-processing is required.

SUMMARY OF THE INVENTION

The object of the invention is thus to adapt an existing three-dimensional reconstruction algorithm in such a way that it can on the one hand be efficiently realized and on the other hand a more simple augmentation of missing projection data in the case of localized defects, for example a truncation or a metal region, is enabled, wherein artifact-reduced three-dimensional reconstruction data sets are obtained.

To achieve this object in the case of a method of the type cited in the preamble, the following steps are provided according to the invention:
  determining of filter lines in the projection images,
  use of a first local transformation along the filter lines on the projection data,
  augmentation of the missing projection data on the transformed projection data,
  use of a non-local transformation different from a ramp filter in such a way that the successive execution of the first local transformation and the non-local transformation creates a ramp filter, for determining of filtered, augmented projection data,
  determining of the three-dimensional image data set by means of back-projection of the filtered, augmented projection data.

The invention thus works on the basis that the areas in which projection data is missing (thus the truncation edges or the projection data which is unusable because of excessively strong attenuation, in particular by means of metals,) are already identified as known. In these areas, projection data is thus completely missing, or at least usable projection data is lacking. The method presented here is based on converting the projection image data prior to the filtering with a local transformation into transformed projection data. As this is a local transformation, the projection defective areas, thus the sub-areas, in the original projection images and in the transformed projection data are identical. The projection defective regions/sub-areas are thus not enlarged, as would be the case with a folding with a non-local kernel, for example a ramp filter. An augmentation of missing information in the domain of the transformed projection data then takes place. The realization of the augmentation is more simply possible than in the domain of the non-transformed projection images, thus of the non-transformed projection data. This then applies in particular, if the first transformation is selected such that, if the projection data along a filter line is regarded as a function, the transformed intermediate function resulting, which is created by using the first local transformation, is thinly populated or smooth by comparison with the original function.

In order to generate the filtered projection data which is ultimately required, the augmented, transformed projection data is then folded with a non-local kernel along the filter lines, which takes place within the framework of the non-local transformation. The kernels of the transformations are here selected in such away that if the transformations are applied successively, the ramp filtering along the filter lines is once again yielded.

The three-dimensional back-projection of the filtered, augmented projection data into the volume for determining of the three-dimensional image data set, can then take place as generally known and need not be further set out here.

It should be mentioned at this point that of course in the case of the inventive algorithm too, a weighting of the projection images, in particular a redundancy weighting, can take place as known, prior to the steps.

The fundamental idea of the present invention thus lies in adapting a present reconstruction algorithm such that it delivers artifact-reduced results from projection data with localized defects, for example a truncation or a metal region, without here performing explicit data interpolation or extrapolation in the projection data domain. Instead, an augmentation, for example by means of interpolation or extrapolation or also setting of the projection data in the subareas to a particular value in the domain of the transformed projection data is provided, where such a step is more easily possible. In the case of the folding of the projection data the original kernel, thus the ramp filter, is no longer used here, but this comes into being only by means of the combination of the first local transformation with the non-local transformation.

Such an adjustment of such a basically known filtered back-projection algorithm is simple and efficient to implement, and in addition an increase in computing efficiency and simple maintenance of the algorithm are provided. Artifacts are advantageously reduced and the local transformation can be selected such that the projection data augmentation in the subareas can take place in a simpler manner than in the projection data of the original projection images.

It should at this stage be mentioned that differently modified ramp filters can frequently be selected for adaptation of the image quality, in particular apodized ramp filters, which ultimately result in a "softer" representation. The use of modified ramp filters of this kind does of course lie within the scope of the inventive method represented here, as the corresponding modifications, in particular the apodizing, can ultimately by represented by means of apodizing functions (or generally modification functions) to be applied to the data. These can be used during the method, particularly preferably however within the framework of the non-local transformation. The term ramp filter, as used within the context of the present invention, thus also comprises filter kernels modified in this way, in particular apodized filter kernels.

As already mentioned, it can be provided for that the augmentation of the missing projection data takes place by means of interpolation and/or extrapolation or by means of setting the missing projection data to a predefined value, in particular 0. While it is thus basically possible to apply simple interpolation and/or extrapolation methods on the transformed projection data too, skilled selection of the first local transformation provides the possibility of simply setting the missing projection data in the transformed projection data to a predefined value, in particular 0. This is examined in greater detail below.

In a particularly advantageous embodiment of the present invention it can be provided for that the first local transformation is a derivation, in particular the first derivation, along the filter lines and/or the non-local transformation is a Hilbert transformation. In contrast to the ramp filtering, a derivation is a local operation, which can thus be performed precisely in the vicinity of the sub-area, for example the truncation edge and/or the metal region. A Hilbert transformation can then be used as non-local transformation, which is based on the knowledge that the ramp filtering is essentially equivalent to the successive execution of derivation and Hilbert transformation. The derivation can here particularly advantageously take place according to the finite differences method, in particular with the use of at least two sampling points. In this way a high level of locality and, in particular when taking account of two sampling points, a high degree of efficiency is enabled. Furthermore it can particularly expediently be provided that for augmentation of the missing projection data, the transformed projection data is set to 0 in the sub-area. In internal subareas, thus for example in metal regions, the derivation values are therefore initialized to 0, outside the detector surface they are implicitly assumed to be 0. Thus in these regions there is an implicit assumption of an unchanging projection data value, which however advantageously never needs to be explicitly calculated, as was still necessary in the prior art. No explicit estimation of missing projection data values is thus necessary, which stems from the fact that ultimately one power is "saved" in the derivation. It should be mentioned at this point that higher derivations too are entirely conceivable, for example second derivations, in which by means of constant assumption of the second derivations, a linear dependence of the projection data in the subareas in the actual space of the projection images can even be assumed, without these being explicitly specified.

In a further embodiment of the present invention it can be provided for that a second local transformation is applied to the augmented projection data, before the non-local transformation takes place, wherein the successive execution of the first local transformation, the second local transformation and the non-local transformation yields the ramp filter. An optional second local transformation is thus conceivable, as long as the overall procedure, i.e. the use of all provided transformations once more yields the customary ramp filter. It can for example be provided for that the first local transformation is a local high-pass filter and the second local transformation is a local low-pass filter or conversely the first local transformation is a local low-pass filter and the second local transformation is a local high-pass filter.

As well as the method, the invention also relates to an X-ray device, comprising a control device embodied for execution of the inventive method. With such an X-ray device an improved, more computationally efficient and more easily maintained artifact reduction is thus provided in subareas missing projection data from the projection images. All embodiments relating to the inventive method can thus be transferred analogously to the inventive X-ray device, which can for example be a CT-device.

BRIEF DESCRIPTION OF THE DRAWINGS

Further advantages and details of the present invention are evident from the exemplary embodiments described in the following, and based on the drawing. Wherein.

DETAILED DESCRIPTION OF THE INVENTION

Figure 1:
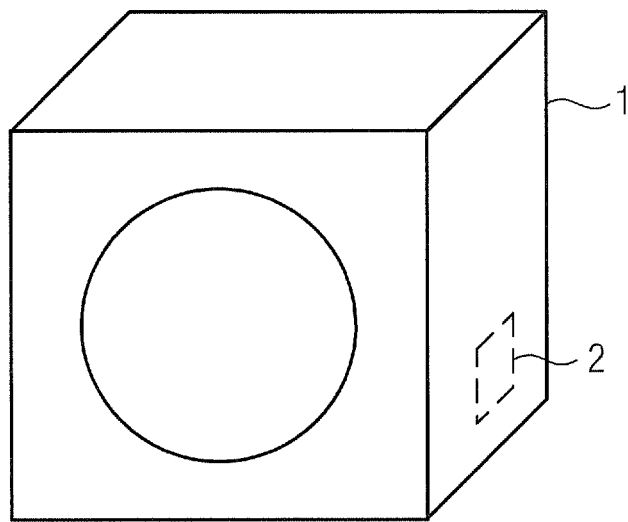
FIG. 1 shows an inventive X-ray device.

FIG. 1 shows an inventive X-ray device 1. This here takes the form of a CT-device (computed tomography device), such as is widely known in the prior art. Here projection images, which in their entirety form projection data, are captured from different projection angles, in order to reconstruct therefrom a three-dimensional image data set of an object to be captured. To this end it can for example be provided that an X-ray emitter and if applicable also an X-ray detector lying opposite each other move on a prescribed capture trajectory, for example a circular path, in order regularly to capture two-dimensional projection images.

The X-ray device 1 now further comprises a control device 2, which controls operation of the X-ray device 1 and is embodied for execution of the inventive method.

Figure 2:
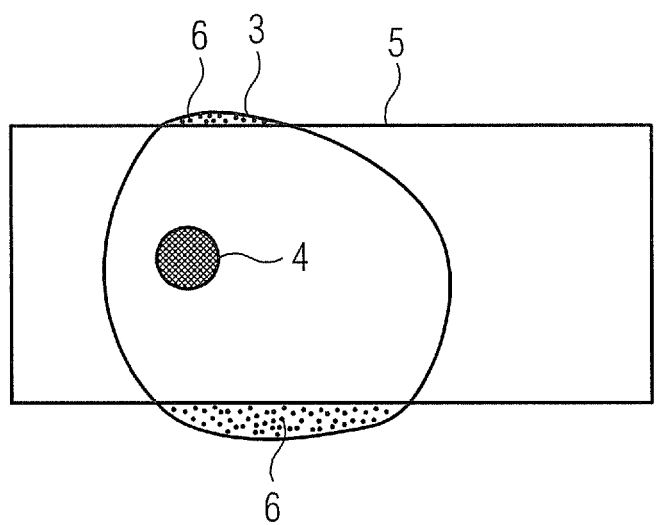
FIG. 2 shows a schematic sketch illustrating subareas of missing projection data.

The inventive method, which is to be described in greater detail below, relates to the most efficient and complete correction of artifacts, which are triggered by means of projection data defects and sub-areas of an object to be represented not captured as a result of truncation. FIG. 2 is here initially examined. An object 3 in its extent is shown there in a schematic sketch. Either enclosed by the object 3 or located in the recording area, the position of a metallic object 4 is further shown in FIG. 2, which as a result of excessively strong attenuation of X-rays results in no usable projection data on the corresponding beam paths. The detector surface is further indicated by 5 in FIG. 2. The object 3 is evidently too high to be fully captured. This means that there are truncation areas 6 represented in dotted form, for which data is likewise missing in the projection images. In the projection direction represented here, the reference characters 4 and 6 thus indicate sub-areas in which no or at least no reusable projection data is present.

The determining of these areas, thus in concrete terms of the truncation edges or the outline of the metallic object 4 respectively, is known in the prior art; however the inventive method now makes available a more efficient and elegant way of augmenting the missing projection data in the identified subareas, in which no projection data of the object 3 is present.

After the projection images have thus if applicable been subjected to a weighting, in particular a redundancy weighting, and the sub-areas are identified, in a step 7 of the inventive method (FIG. 3) the filter lines are determined as basically known in the case of algorithms of the filtered back-projection. In the circular geometry (circular CT) previously addressed, lines running horizontally over the detector are usually selected as filter lines.

In a step 8 a local transformation is then applied to the projection data of the projection images, here a first derivation formed along the filter lines. The finite differences method with the use of two sampling points is employed. A very local operation is thus involved here.

The result obtained is thus transformed projection data 9, the derivation of the original projection data 10.

In a step 11 further processing now takes place on this transformed projection data 9, in that the sub-areas in which projection data is missing are augmented, here, in that this missing projection data is set to 0 in the domain of the transformed projection data, which means that in the metal region 4 and the truncation areas 6 of FIG. 2 the derivation is set to 0. This means however that a constant value is assumed in the domain of the original projection data 10, which however need not be explicitly specified. It should at this point be noted that of course other types of extrapolation interpolation can be used in step 11 in the domain of the transformed projection data 9.

The result after step 11 is thus transformed, augmented projection data 12, to which a non-local transformation, here a Hilbert transformation is then applied in a step 13, wherein the local transformation in step 8 and the Hilbert transformation successively applied in step 13 produce a ramp filter. This means that the non-augmented projection data is ultimately treated precisely as in a conventional method of filtered back-projection, for example the Feldkampf algorithm.

After step 13 filtered, augmented projection data 14 is thus obtained, which is now back-projected in the usual manner in a back-projection step 15 to the desired, artifact-reduced three-dimensional image data set 16. Here, for example the known method from the Feldkamp algorithm is used.

Figure 3:
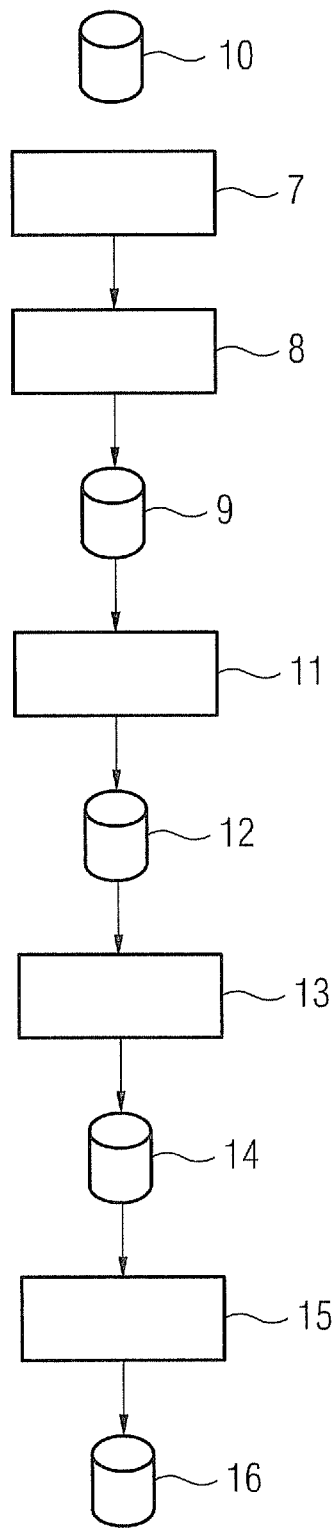
FIG. 3 shows a flow-chart of the inventive method.

It should also be noted at this point that the exemplary embodiment represented in FIG. 3 and just described illustrates the inventive method only based on the example of a first derivation and a Hilbert transformation, but other approaches are certainly conceivable, in which the augmentation of missing projection data is performed only after local transformation of the original projection data 10, wherein the local transformation is part of the filter process in the filtered back-projection.

The invention claimed is:

1. A method for reconstructing a three-dimensional image data set of an object, comprising:
    capturing a plurality of projection images of the object with an X-ray device from different projection angles, wherein no projection data is present in a sub-area of the object lying outside a coverage of the X-ray device or as a result of attenuation;
    determining filter lines in the projection images;
    transforming projection data of the projection images using a first local transformation along the filter lines on the projection images;
    augmenting missing projection data in the sub-area on the transformed projection data;
    determining filtered and augmented projection data using a non-local transformation on the augmented and transformed projection data, wherein the first local transformation and the non-local transformation creates a ramp filter; and
    determining the three-dimensional image data set by back-projection of the filtered and augmented projection data.

2. The method as claimed in claim 1, wherein the augmentation of the missing projection data is obtained by interpolation and/or extrapolation on the transformed projection data.

3. The method as claimed in claim 1, wherein the augmentation of the missing projection data is obtained by setting the missing projection data in the sub-area on the transformed projection data to a predefined value.

4. The method as claimed in claim 3, wherein the predefined value is set to zero.

5. The method as claimed in claim 1, wherein the first local transformation is a derivation along the filter lines.

6. The method as claimed in claim 5, wherein the derivation is a first derivation.

7. The method as claimed in claim 5, wherein the derivation is obtained according to a finite difference method using at least two sampling points.

8. The method as claimed in claim 1, wherein the non-local transformation is a Hilbert transformation.

9. The method as claimed in claim 1, wherein the non-local transformation is different from the ramp filter.

10. The method as claimed in claim 1, wherein a second local transformation is applied to the augmented projection data before the non-local transformation.

11. The method as claimed in claim 10, wherein the first local transformation, the second local transformation, and the non-local transformation creates the ramp filter.

12. The method as claimed in claim 10, wherein the first local transformation is a local high-pass filter and the second local transformation is a local low-pass filter.

13. The method as claimed in claim 10, wherein the first local transformation is a local low-pass filter and the second local transformation is a local high-pass filter.

14. The method as claimed in claim 1, wherein the attenuation is caused by a metal.

15. An X-ray device, comprising:
an X-ray detector for capturing a plurality of projection images of the object with an X-ray device from different projection angles, wherein no projection data is present in a sub-area of the object lying outside a coverage of the X-ray device or as a result of attenuation; and
a control device for:
 determining filter lines in the projection images;
 transforming projection data of the projection images using a first local transformation along the filter lines on the projection images;
 augmenting missing projection data in the sub-area on the transformed projection data;
 determining filtered and augmented projection data using a non-local transformation on the augmented and transformed projection data, wherein the first local transformation and the non-local transformation creates a ramp filter; and
 determining the three-dimensional image data set by back-projection of the filtered and augmented projection data.

* * * * *